(12) United States Patent
Ghorpade et al.

(10) Patent No.: US 6,417,374 B1
(45) Date of Patent: Jul. 9, 2002

(54) PROCESS FOR THE PREPARATION OF BETA HYDROXY-DELTA LACTONE USING NOVEL INTERMEDIATES

(75) Inventors: Sandeep Raghunath Ghorpade; Uttam Ramrao Kalkote; Subhash Prataprao Chavan; Sunil Ramchandra Bhide; Thottappillil Ravindranathan, all of Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/783,749

(22) Filed: Feb. 15, 2001

(51) Int. Cl.$^7$ .................................................. C07F 7/02
(52) U.S. Cl. ........................ 549/214; 560/128; 556/482
(58) Field of Search .......................... 549/214; 556/482; 560/128

Primary Examiner—Amelia Owens
(74) Attorney, Agent, or Firm—Ladas & Parry

(57) ABSTRACT

The present invention relates to a process for the preparation of optically active 6-hydroxymethyl-4-(tert-butyldimethylsilyloxy)-(4R,6S)-tetrahydro-2H-2-pyranone (β-Hydroxy-δ-lactone) an important intermediate in the synthesis of biologically active drugs e.g. compactin, atorvastatin, fluvastatin, cholesterol lowering drugs.

11 Claims, No Drawings

PROCESS FOR THE PREPARATION OF BETA HYDROXY-DELTA LACTONE USING NOVEL INTERMEDIATES

This invention relates to a process for the preparation of optically active 6-hydroxymethyl-4-(tert-butyldimethylsilyloxy)-(4R,6S)-tetrahydro-2H-2-pyranone (β-hydroxy-δ-lactone) having formula 1.

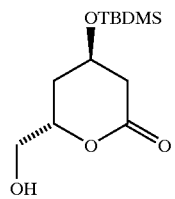

1

More particularly it relates to a process for the preparation of the said compound using Cis,cis-3,5-di(methylcarbonyloxy)cyclohexylacetate having formula 2

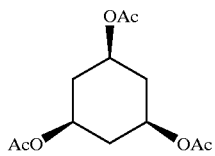

2

The compound β-hydroxy-δ-lactone (1) is an important intermediate in the synthesis of biologically active drugs e.g. compactin, atorvastatin, fluvastatin, cholesterol lowering drugs.

Hitherto known processes for the synthesis of β-hydroxy-δ-lactone (1) involves a) Addition of lithium enolate of ethylacetate to (S)-2,2-dimethyl-1,3-dioxalane-4-ethanol, which in derived from L-malic acid, followed by acid treatment. (T. Rosen, M. J. Taschner & C. H. Heathcock, *J. Org. Chem.*, 1984, 49, 3994–4003)

b) Multistep chemical manipulation of tri-acetyl-D-glucal (T. Rosen, M. J. Taschner, C. H. Heathcock, *J. Org. Chem.*, 1984, 49, 3994; F. G. Kathawala, Mountain Lake N. J. *USP* 4739,073)

c) Coupling of (S)-2,2-dimethyl-1,3-dioxalane-4-ethanal with optically active (R)-methyl-p-tolylsulphoxide which in turn obtained by oxidation of methyl-p-tolysulphide with baker yeast, followed by desulphurization and few chemical manipulation (J. Beecher, I. Brackerridge, S. M. Roberts, J. Tang & A. J. Willetts, J. Chem. Soc. Perkin Tran.I 1995, 1641; *Tetrahedron* 1995, 51, 13217)

d) Deprotection and hydrolysis of 6-cyanomethyl-2,2-dimethyl-1,3-dioxane-4-acetate, which in turn obtained by two carbon homologation on optically active ethyl-3-hydroxy-4-cyanobutyrate and followed by stereoselective reduction (P. L. Brower, D. E. Butler, C. F. Deering, T. V. Le, A. Millar, T. N. Nanninga & B. D. Roth, *Tet. Lett*, 1992, 33, 2279–82)

e) Racemic and optically active β-hydroxy-δ-lactone from cis-cyclohexane-1,3,5-triol (K. Prasad & O. Repic, *Tet. Lett.*, 1984, 25, 2435–38; H. Suemune, M. Takahashi, S. Maeda, Z. Fxi & K. Sakai, *Tet. Asymm.* 1990, 1, 425–8, M. Canda, V. Eyken & M. Vandewalle, *Tet. Asymmetry* 1990, 1, 17–20).

f) Enzymatic kinetic resolution of racemic β-hydroxy-δ-lactone by transesterification with vinyl acetate in THF using *Chromobacteriun viscosum* lipase as catalyst at 40° C. [Crosby, J. B.; Andrew, J. H.; John, A. L. WO 9306235 A1 CA 119:936292 (1993)]

g) Chemoenzymatic route involving kinetic resolution through lactone formation in ether catalyzed by PPL [Bonini, C.; Pucci, P.; Viggiani, L. *J. Org. Chem.* 1991, 56, 4050]

h) Chemoenzymatic route involing enzymatic desymmetrization of intermediate diacetate, followed by chemical conversions. [Bonni, C.; Racioppi, R.; Righi, G.; Viggiani, L. *J. Org. Chem.* 1991, 58, 802]

i) Chemoenzymatic synthesis starting from endohydroxy-lacto which is obtained by enzymatic resolution [MaCague, R.; Olivo, H. F.; Roberts, S. M. *Tetrahedron Lett.* 1993, 34, 3785]

j) Diastereoselective synthesis of lactone based on Eu(fod)$_3$ catalyzed highly diastereoselective [4+2] cycloaddition of 1-methoxybuta-1,3-diene to (2R)-N-glyoxyloxyborane-10,2-sultam and further chemical transformations [Bauer, T.; Kozak, J.; Chauis, C.; Jurczak, J. *J. Chem. Soc.; Chem. Commun.* 1990, 1178 and *Tetrahedron: Asymmetry* 1996, 7, 1391]

k) Chiral synthesi using (R)-O-benzylglycidol as starting material [Takano, S.; Shimazaki, Y.; Sekiguchi, Y.; Ogasawara, K. *Synthesis* 1989, 539]

l) Asymmetric synthesis based on Red-Al promoted intramolecular reductive cleavage of Benzyl 4-hydroxy-2-butenyl ether structures. [Hatakeyama, S.; Satoh, K.; Takano, S. *Tetrahedron Lett.* 1993, 34, 7425]

The prior art processes have following drawbacks:

1. The processes use chemicals such as butyl lithium, lithium aluminum hydride, methoxy-diethylborane which are costly and difficult to handle and therefore make the process difficult.

2. All known process are however involves large number of synthetic steps resulting in low over all yields.

The main object of the present invention is to provide a new process for the preparation of β-hydroxy-δ-lactone (1), which obviates the drawbacks of the prior art processes and use cheaper and easily accessible chemicals.

Another object of the present invention is to provide (i) selective Baeyer-Villiger rearrangement of 3-hydroxy-5-t-butyldimethylsilyloxy-1-cyclohexanone (9) with chemical reagent or Baeyer Villiger oxidase and (ii) enantioselective hydrolysis of cis-3-(methylcarbonyloxy)-5-(tert-butyldimethylsilyloxy)cyclohexylacetate with enzyme.

DETAILED DESCRIPTION OF THE INVENTION

Accordingly the present invention provides a process for the preparation of β-hydroxy-δ-lactone of formula 1 using novel intermediates which comprises a) reacting a compound of formula 2 with a lipase enzyme in a buffer having

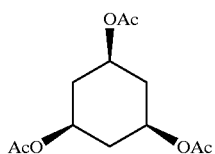
2 pH ranging between 5 to 7, at a temperature ranging from 25 to 30° C. for a period ranging between 19 to 30 hrs. extracting the reaction mixture with an organic solvent, removing the solvent by evaporation to obtain cis,cis-3-hydroxy-5-methylcarbonyloxy-cyclohexylacetate having formula (3),

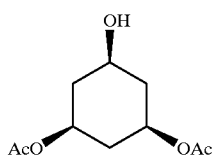
3 b) reacting a compound of formula 3 with tert-butyldimethylsilylchloride in an organic solvent in the presence of an organic base at a temperature ranging from −15 to 20° C. for a period ranging from 6 to 12 hrs, separating the organic solvent, to obtain cis,cis-3-(methylcarbonyloxy)-5-(tert.butyldimethylsilyloxy) cyclohexylacetate having formula 4,

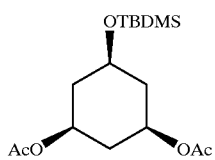
4 c) reacting a compound 4 with a lipase enzyme in a buffer having pH in the range of 5 to 8, at a temperature ranging from 25 to 30° C. for a period ranging between 24 to 60 hrs., extracting the mixture with an organic solvent, removing the solvent by evaporation and on column chromatography to obtain 3-hydroxy-5-(tert.butyldimethylsilyloxy)-(1S,3R,5R)-cyclohexylace-tate having formula 5,

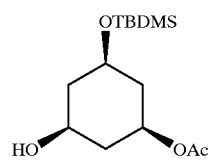
5 d) reacting a compound of formula 5 with dihydropyran in an organic solvent in the presence of p-toluene sulphonic acid at a temperature ranging from 5 to 10° C. for a period ranging from 2 to 5 hrs, quenching the above reaction with an aqueous sodium bicarbonate, separating the organic layer, drying, on evaporating and column chromatography to obtain 3-tetrahydro-2H-2-pyranyloxy-5-(tert.butyldimethylsilyloxy)-(1S,3R,5R)-cyclohexylacetate having formula 6,

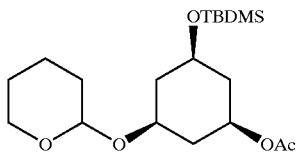
6 e) reacting a compound of formula 6 with an anhydrous potassium carbonate in methanol at room temperature for a period ranging from 2 to 6 hrs, evaporating the solvent, extracting with an organic solvent, washing with brine solution, drying, evaporating and column chromatography to obtain 3-tetrahydro-2H-2-pyranyloxy-5-(tert.butyldimethylsilyloxy)-(1S,3R,5R)-cyclohexan-1-ol having formula 7,

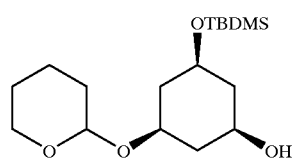
7 f) reacting a compound of formula 7 with pyridinium chlorochromate in an organic solvent at room temperature for a period ranging from 6 to 8 hours, extracting the above mixture with an ether, washing with brine, drying, on evaporating and column chromatography to obtain 3-tetrahydro-2H-2-pyranyloxy-5-(tert.butyldimethylsilyloxy)-(1S,3R,5R)-cyclohexan-1-one having formula 8,

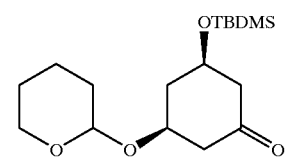
8 g) reacting a compound of formula 8 with magnesium bromide in an organic solvent at a temperature ranging from 5 to 30° C. for a period ranging from 1 to 12 hours, quenching the above reaction ammonium chloride, separating the organic layer, drying and on evaporating to obtain 3-hydroxy-5-(tert-butyldimethyl silyloxy)-(3S,5R)-cyclohexan-1-one having formula 9,

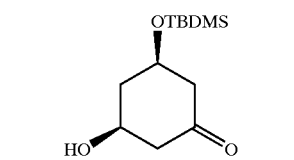
9 h) reacting a compound of formula 9 with m-chloroperbenzoic acid at room temperature for a period ranging from 16–24 hours, extracting the compound with an orgainc layer, washing with sodium metabisulphite, brine, drying and on evaporation to obtain 6-hydroxymethyl-4-(tert-butyldimethylsilyloxy)-(4R,6S)-tetrahydro-2H-2-pyranone having formula 1.

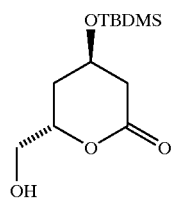

1

In an embodiment of the present invention the organic solvent used in steps a, c, e and h for the extraction of the product is selected from the group consisting of ethyl acetate, chloroform, dichloromethane and t-butanol.

In an another embodiment of the present invention the organic solvent used in steps b, e, f and g for the reaction is selected from the group consisting of ethyl acetate, chloroform, dichloromethane, methanol and diethyl ether.

In yet another embodiment of the present invention the organic base used in step b for the reaction is selected from triethylamine and pyridine.

In yet another embodiment of the present invention the buffer used in steps a and c for the reaction is selected from phosphate buffer and citrate buffer.

In still another embodiment of the present invention the lipase used in steps a and c for the reaction is selected from the group consisting of pig procain lipase (PPL), pig liver esterase (PLE) and chicken liver acetone powder (CLAP).

In yet another embodiment the present invention provides a compound cis,cis-3-hydroxy-5-methylcarbonyloxy-cyclohexylacetate having formula (3),

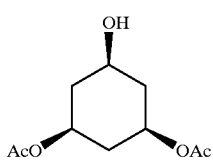

3

In yet another embodiment the present invention provides a compound cis,cis-3-(methylcarbonyloxy)-5-tert.butyldimethylsilyloxy)cyclohexylacetate having formula 4,

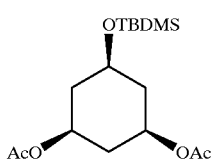

4

In yet another embodiment the present invention provides a compound 3-hydroxy-5-(tert.butyldimethylsilyloxy)-(1S,3R,5R)-cyclohexylacetate having formula 5,

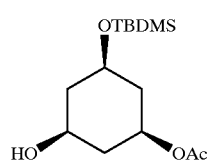

5

In yet another embodiment the present invention provides a compound 3-tetrahydro-2H-2-pyranyloxy-5-(tert.butyldimethylsilyloxy)-(1S,3R,5R)-cyclohexylacetate having formula 6,

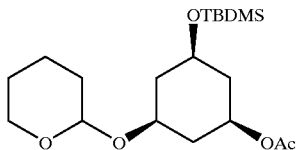

6

In yet another embodiment the present invention provides a compound 3-tetrahydro-2H-2-pyranyloxy-5-(tert.butyl dimethylsilyloxy)-(1S,3R,5R)cyclohexan-1-ol having formula 7,

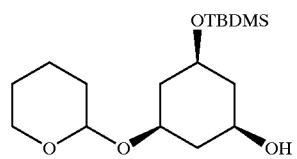

7

In yet another embodiment the present invention provides a compound 3-tetrahydro-2H-2-pyranyloxy-5-(tert.butyldimethylsilyloxy)-(1S,3R,5R)-cyclohexan-1-one having formula 8,

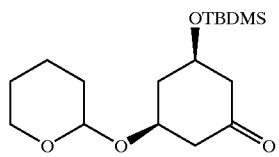

8

In yet another embodiment the present invention provides a compound 3-hydroxy-5-(tert-butyldimethylsilyloxy)-(3S,5R)-cyclohexan-1-one having formula 9,

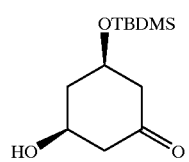

9

Cis,cis-3,5-di(methylcarbonyloxy)cyclohexylacetate (2) is prepared by treatment of acetic anhydride with cis-1,3,5-cyclohexantriol which is made by known literature procedure (Strong, P. N.; Keana, J. F. W. *J Org. Chem.* 1975, 40, 956).

The process of the present invention is described hereinbelow with references to the following examples, which are illustrative only and should not be construed to limit the scope of the present invention in any manner.

EXAMPLE 1

Preparation of cis,cis-3-hydroxy-5-methylcarbonyloxy-cyclohexylacetate 3

Finely powdered cis,cis-3,5-di(methylcarbonyloxy) cyclohexylacetate 2 (6.5 parts, 25.19 mmol parts) was suspended in 0.1 M sodium phosphate buffer (pH 7) (135 parts) and stirred vigorously. To the stirred suspension Porcine Liver Esterase (0.110 parts) was added and reaction mixture was stirred vigorously at 30° C. for 20 hr. pH of the reaction mixture was monitored at every 2 hrs and was maintained at pH 7 using 1N NaOH solution. After completion of reaction (20 hr), it was extracted with ethyl acetate (2×150 parts). Organic layers were combined and washed with brine, dried on anhydrous sodium sulfate and concentrated under vacuum to yield cis,cis-3-hydroxy-5-methylcarbonyloxycyclohexylacetate 3 yield (4.8 g parts, 88%).

1H NMR(CDCl$_3$): δ1.20–1.58 (qn, 3H), 2.08 (s, 6H), 2.28 (m, 3H),3.78 (m, 1H), 4.78 (m, 2H) 13C NMR (CDCl$_3$): δ21.15, 36.33, 39.93, 64.83, 67.65, 170.42 IR (KBr): 754.60, 884.15, 1029.29, 1140.34, 1250.00, 1367.64, 1738.92, 2871.17, 2953.14, 3445.47 Mass: Base m/e=96 other m/e: 156, 138, 114, 73, 67, 67, 60, 55 Elemental analysis: calculated for $C_{10}H_{16}O_5$: C 55.56%, H 7.40% Found: C 55.30%, H 8.00%

EXAMPLE 2

Preparation of cis,cis-3-(methylcarbonyloxy)-5-(tert.butyldimethylsilyloxy)cyclohexylacetate 4

Cis,cis-3-hydroxy-5-methylcarbonyloxy-cyclohexylacetate (3, 2 parts, 9.26 mmol) and DMAP (0.113 parts, 0.926 mmol) were placed in 100 ml two-necked round bottom flask equipped with dropping funnel and two-way stopcock. It was evacuated and flushed with argon. To it, dry dichloromethane (10 parts) and dry HMPA (2 part) was added and stirred to dissolve. The solution was cooled to −10° C. with stirring. To it, solution of tert-butyldimethylsilyl chloride in 10 part dry dichloromethane was added dropwise while maintaining temperature below 0° C. Reaction mixture was stirred for 15 min and to it dry triethylamine (2.02 g, 20 mmol) was added dropwise. Reaction mixture was stirred at room temperature for 12 hr. It was then transferred to a separating funnel and washed successively with cold, dil. HCl water, aq. NaHCO$_3$ and then brine. Organic layer was dried on anhydrous sodium sulfate and solvent was removed under vacuum. Residue was purified by flash column chromatography. (eluent 2–4% ethyl acetate in petroleum ether) to yield Cis,cis-3-(methylcarbonyloxy)-5-(tert.butyldimethylsilyloxy)cyclohexylacetate (4, yield 2.85 parts, 90%).

$^1$H NMR (CDCl$_3$): δ0.06(s, 9H), 0.87 (s, 6H), 1.20–1.45 (m, 3H), 2.03 (s, 6H), 2.2 (m, 3H), 3.38 (m, 1H), 4.73 (m, 2H). 2.3 $^{13}$C NMR (CDCl$_3$): δ−5.07, 17.61, 25.40, 36.17, 40.40, 65.43, 67.01, 169.64 IR (CHCl$_3$): 758.90, 838.05, 1034.91, 1106.32, 1246.82, 1368.91, 1734.01, 2858.81, 2955.07 Mass: Base m/e=117 other m/e: 273, 213, 171, 159, 129, 117, 97, 79, 75, 57 Elemental analysis: calculated for $C_{26}H_{30}O_5Si$: C 58.185%, H 9.10% Found: C 58.19%, H 9.50%

EXAMPLE 3

Preparation of 3-hydroxy-5-(tert.butyldimethylsilyloxy)-(1S,3R,5R)-cyclohexylacetate (5)

Cis,cis-3-(methylcarbonyloxy)-5-(tert.butyldimethylsilyloxy)cyclohexylacetate (4, 5 patrs, 147 mmol) was dissolved in tert-butanol (20 parts). To the solution, 0.1 M sodium phosphate buffer (230 parts, pH 8) was added and mixture was stirred vigorously. To the stirred emulsion, Porcine liver esterase (0.150 parts) was added and the mixture was stirred vigorously at 30° C. for 54 hrs. During reaction pH was maintained at 8 using 1N sodium hydroxide solution. Reaction mixture was extracted with ethyl acetate (3×200 parts). Organic layers were combined and washed with brine. It was then dried on anhydrous sodium sulfate and solvent was removed under vacuum. Oily residue contained 3-hydroxy-5-(tert.butyldimethylsilyloxy)-(1S,3R,5R)-cyclohexylacetate 5 along with unreacted 4. Both were separated by flash column chromatography. Cis,cis-3-(methylcarbonyloxy)-5-(tert.butyldimethylsilyloxy)cyclohexylacetate recovered: 1.07 parts; 3-hydroxy-5-(tert.butyldimethylsilyloxy)-(1S, 3R,5R)-cyclohexylacetate (5, yield 2.8 parts, 70% based on recovered starting material.

$^1$H NMR (CDCl$_3$): δ0.06 (s, 9H), 0.87 (s, 6H), 1.35–1.60, (m, 3H), 2.06 (s, 3H), 2.15 (m, 3H), 3.7 (m, 2H), 4.75 (m, 1H) $^{13}$C NMR (CDCl$_3$): δ−4.60, 18.15, 21.38, 25.90, 39.98, 40.31, 43.93, 65.45, 66.40, 68.17, 170.68 IR (CHCl$_3$): 758.43, 838.93, 1049.42, 1109.15, 1218.09, 1254.01, 1370.09, 1725.03, 2859.8, 2887.95, 2952.33, 3017.48 Mass: Base m/e=75 other m/e: 231, 171, 129, 117, 105, 97, 79, 75, 67, 59 Elemental analysis: calculated for $C_{14}H_{28}O_4Si$: C 58.33%, H 9.72% Found: C 58.15%, H 10.20%

Specific rotation [α]$_D$=−4.8 (c 1, CHCl$_3$) e.e. >95% (determined by chiral HPLC of corresponding Mosher ester. Column: Whelk-O1 [4.0 mm Id×25 cm] AT-256; λ=254 nm, flow rate: 1 ml/min; mobile phase: Hexane:isopropanol 98:02; retention time for Mosher ester of 5=4.59, for Mosher ester of ent-5=4.34).

EXAMPLE 4

Preparation of 3-tetrahydro-2H-2-pyranyloxy-5-(tert.butyldimethylsilyloxy)-(1S,3R,5R)-cyclohexylacetate (6)

3-hydroxy-5-(tert.butyldimethylsilyloxy)-(1S,3R,5R)-cyclohexylacetate (5, 2.9 parts, 9.73 mmol) was dissolved in dry dichloromethane (30 parts). The solution was cooled below 0° C. in ice-salt bath. To the stirred solution, dihydropyran (1 part, 12 mmol) was added and p-toluenesulfonic acid monohydrate (0.1 part) was added as catalyst. Reaction mixture was stirred at −10° C. for 2 hr. Reaction was quenched by adding aqueous sodium bicarbonate solution. Both the layers were separated. Aqueous layer was extracted dichloromethane (10 part). Organic layers were combined and washed with water followed by brine wash. It was then dried on anhydrous sodium sulfate and solvent was removed under vacuum. Residue was purified by flash column chromatography to yield 3-tetrahydro-2H-2-pyranyloxy-5-(tert.butyldimethylsilyloxy)-(1S,3R,5R)-cyclohexylacetate 6 (yield 3.7 parts, 99.5%).

$^1$H NMR (CDCl$_3$): δ0.07 (s, 6H), 0.87 (s, 9H), 1.25–1.90 (m, 9H), 204 (s, 3H), 2.05–40 (m, 3H), 3.40–3.75 (m, 3H), 3.86 (m, 1H), 4.55–4.80 (m, 2H) $^{13}$C NMR (CDCl$_3$): δ−4.90, 18.00, 19.40, 19.50, 25.20, 25.80, 30.90, 36.80, 40.70, 41.00, 42.80, 62.00, 62.50, 66.00, 68.00, 69.70, 95.00, 96.80 IR (CHCl$_3$): 752.08, 768.22, 838.35, 1029.76, 1114.56, 1215.63, 1251.94, 1727.19, 2858.86, 2950.80, 3016.74 Mass: Base m/e=85 other m/e: 231, 211, 171, 159, 129, 117, 105, 101, 85, 79, 75, 67, 55 Elemental analysis: calculated for $C_{19}H_{36}O_5Si$: C 61.29%, H 9.68% Found: C 61.37%, H 10.03% Specific rotation [α]$_D$=+1.39 (c 1, CHCl$_3$)

EXAMPLE 5

Preparation of 3-tetrahydro-2H-2-pyranyloxy-5-(tert.butyldimethylsilyloxy)-(1S,3R,5R)-cyclohexan-1-ol (7)

3-tetrahydro-2H-2-pyranyloxy-5-(tert.butyldimethylsilyloxy)-(1S,3R,5R)-cyclohexylacetate (6, 3.5 parts, 9.16 mmol) was dissolved in dry methanol (25 parts). To the solution anhydrous potassium carbonate (0.828 parts, 6 mmol) was added and the mixture was stirred at room temperature for 2 hr. Methanol was removed under vacuum and residue was extracted several times with dichloromethane. Dichloromethane layers were combined and washed with water followed by brine wash. It was dried on anhydrous sodium sulfate. Solvent was removed under vacuum and residue was purified by flash column chromatography to yield 3-tetrahydro-2H-2-pyranyloxy-5-(tert.butyldimethylsilyloxy)-(1S,3R,5R)-cyclohexan-1-ol (7, yield 3 parts, 96%).

$^1$H NMR (CDCl$_3$): δ0.06 (s, 6H), 0.87 (s, 9H), 1.35–1.90 (m, 10H), 2.05–2.35 (m, 3H), 3.40–3.75 (m, 4H), 3.80–3.98 (m, 1H), 4.73 (s, 1H) $^{13}$C NMR (CDCl$_3$): δ–4.90, 18.00, 19.50, 25.20, 25.80, 30.90, 40.00, 40.70, 42.00, 42.30, 44.70, 62.00, 62.50, 65.80, 66.90, 69.50, 70.00, 96.40, 96.80 IR (CHCl$_3$): 753.06, 766.83, 838.54, 867.39, 1020.84, 1048.02, 1114.23, 1215.02, 1253.72, 2858.73, 28884.47, 2947.49, 3013.80, 3418.48 Mass: Base m/e=75 other m/e: 309, 189, 171, 129, 119, 101, 85, 79, 75, 67, 55 Elemental analysis: calculated for C$_{17}$H$_{34}$O$_4$Si: C 61.82%, H 10.30% Found: C 61.83%, H 11.00% Specific rotation [α]$_D$=+0.93 (c 1, CHCl$_3$)

EXAMPLE 6

Preparation of 3-tetrahydro-2H-2-pyranyloxy-5-(tert.butyldimethylsilyloxy)-(3R,5R)-cyclohexan-1-one (8)

3-tetrahydro-2H-2-pyranyloxy-5-(tert.butyldimethylsilyloxy)-(1S,3R,5R)cyclohexan-1ol (7, 2.85 parts, 8.38 mmol) was dissolved in dry dichloromethane (25 parts) under argon atmosphere. To it, anhydrous sodium acetate (0.2 part, 2.6 mmol) and pyridinium chlorochromate (13 part, 2.6 mmol) were added in one portion and the mixture was stirred under argon atmosphere for 8 hr. Then reaction mixture was diluted with diethyl ether (30 parts) and stirred well. The solution was decanted and the remaining black tar was extracted with diethyl ether (13×15 parts). Organic layers were combined and were filtered through small ceilite bed. Then, the organic layer was washed with water (3×20 parts) followed by brine wash. Then it was dried on anhydrous sodium sulfate and solvent was removed under vacuum. Residue was purified by flash column chromatography. Yield of 3-tetrahydro-2H-2-pyranyloxy-5-tert.butyldimethylsilyl oxy)-(3R,5R)-cyclohexan-1-one (8, 2.24 parts, 80%).

$^1$H NMR (CDCl$_3$): δ0.07 (s, 6H), 0.87 (s, 9H), 1.35–1.95 (m, 8H), 2.2–2.8 (m, 4H), 3.50 (m, 1H), 3.85 (m, 3H), 4.60 & 4.75 (2s, 1H) $^{13}$C NMR (CDCl$_3$): δ–4.9, 18.0, 19.5, 19.9, 25.8, 26.0, 30.9, 41.0, 42.5, 47.0, 48.5, 51.5, 62.5, 63.0, 69.0, 69.8, 97.5, 206.5, 207.0 IR (CHCl$_3$): 858.87, 980.49, 1028.79, 1053.00, 1254.14, 1360.70, 1377.86, 1462.85, 1717.24, 2857.60, 2892.24 Mass: Base m/e=187, 85 other m/e: 271, 227, 169, 159, 143, 127, 95, 75, 67 Elemental analysis: calculated for C$_{17}$H$_{32}$O$_4$Si: C 62.19%, H 9.75% Found: C 61.9%, H 10.10% Specific rotation [α]$_D$=+3.71 (c 1, CHCl$_3$)

EXAMPLE 7

Preparation of 3-hydroxy-5-(tert-butyldimethylsilyloxy)-(3S,5R)-cyclohexan-1-one (9)

3-tetrahydro-2H-2-pyranyloxy-5-(tert.butyldimethylsilyloxy)-(3R,5R)-cyclohexan-1-one (8, 1 part, 2.959 mmol) was placed in 50 parts two necked round bottom flask equipped with two-way stopcock and rubber septum. Flask was evacuated and flushed with argon. To it, dry ether (10 parts) was added and the resulting solution was stirred vigorously. To the stirred solution magnesium bromide etherate (2.3 parts, 8.9 mmol) was added and the mixture was stirred for 10 hr. The reaction mixture was cooled in ice-bath and reaction was quenched by adding saturated ammonium chloride solution. Both the layers were separated. Aqueous layer was extracted with ether (2×10 parts). Organic layers were combined and washed with brine. Then it was dried on anhydrous sodium sulfate and solvent was removed under vacuum. Residue was purified to yield 3-hydroxy-5-(tert-butyldimethylsilyloxy)-(3S,5R)-cyclohexan-1-one (9, 0.67 parts, 89%).

$^1$ H NMR (CDCl$_3$): δ0.10 (s, 6H), 0.88 (s, 9H), 1.95–2.30 (m, 2H), 2.45–2.78 (m, 4H), 3.95 (d, 1H), 4.36 (m, 1H), 4.56 (m, 1H) $^{13}$C NMR (CDCl$_3$): δ–5.28, –5.50, 17.55, 25.34, 38.24, 49.56, 49.89, 68.86, 70.48, 206.78 IR (CHCl$_3$): 777.13, 835.81, 1010.66, 1045.71, 1095.81, 1254.55, 1381.17, 1413.71, 1464.09, 1715.72.2857.70, 2892.64, 2932.26, 2951.84, 3439.28 Mass: Base m/e=75 other m/e: 187, 169, 145, 129, 101, 95, 75, 69, 59 Elemental analysis: calculated for C$_{12}$H$_{24}$O$_3$Si: C 59.01%, H 9.83% Found: C 58.65%, H 10.18% Specific rotation [α]$_D$=+16.20 (c 1, CHCl$_3$)

EXAMPLE 8

Preparation of 6-hydroxymethyl-4-(tert-butyldimethylsilyloxy)-(4R,6S)-tetrahydro-2H-2-pyranone (1)

3-Hydroxy-5-(tert-butyldimethylsilyloxy)-(3S,5R)-cyclohexan-1-one (9, 0.1 part, 0.394 mmol) and 50% 3-chloroperbenzoic acid (0.275 parts, 0.79 mmol) were mixed and kept in dark for 24 hr. Reaction mixture was dissolved in ethyl acetate and washed successively with sodium metabisulfite solution, sodium bicarbonate solution followed by brine wash. It was then dried on anhydrous sodium sulfate and solvent was removed under vacuum. Residue was purified by flash column chromatography to yield white, crystalline 6-hydroxymethyl-4-(tert-butyldimethylsilyloxy)-(4R,6S)-tetrahydro-2H-2-pyranone (1, yield 0.035 part, 50%).

1H NMR (CDCl$_3$): δ0.09, 0.07 (2s, 6H), 0.87 (s, 9H), 1.63 (bs, 1H), 1.74–1.9 (m, 2H), 2.59 (d, 2H, J=3), 3.65 (dd, 1H, J=3, 12), 3.88 (dd, 1H, J=3, 12), 4.36 (m, 1H), 4.79 (m, 1H) 13C NMR (CDCl$_3$): δ–4.93, 17.93, 25.68, 32.15, 39.26, 63.61, 64.59, 77.07, 170.1 IR (CHCl$_3$): 666.31,898.12, 1021.88, 1061.06, 1086.17, 1118.98, 1390.84, 1463.17, 1729.43, 2857.28, 3418.25 Mass: Base m/e=75 other m/e: 260, 229, 203, 185, 161, 143, 129, 111, 101, 69,59 Elemental analysis: calculated for C$_{12}$H$_{24}$O$_4$Si: C 55.38%, H 9.20% Found: C 55.42%, H 9.03% Specific rotation [α]$_D$=+3.0 (c 1, CHCl$_3$) before crystallization e.e. 86% [α]$_{D=+}$1.9 (c 1, CHCl$_3$) after recrystallization e.e 98%

(determined by chiral HPLC of corresponding benzoate derivative, column-Whelk-O1 [4.0 mm Id×25 cm] AT-256; λ=254 nm, flow rate: 1 ml/min; mobile phase: Hexane:isopropanol 92:08; retention time for benzoate of 1=17.48, for benzoate of ent-1=20.10).

We claim:

1. A process for the preparation of 6-hydroxymethyl-4-(tert-butyldimethylsilyloxy)-(4R,6S)-tetrahydro-2H-2-pyranone of formula 1 wherein the said process comprising:

(a) reacting a compound of formula 2 with a lipase enzyme in a buffer having

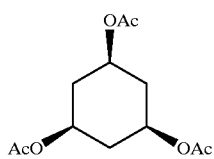

2 pH ranging between 5 to 7, at a temperature ranging from 25 to 30° C. for a period ranging between 19 to 30 hrs. extracting the reaction mixture with an organic solvent, removing the solvent by evaporation to obtain cis,cis-3-hydroxy-5-methylcarbonyloxy-cyclohexylacetate having formula (3),

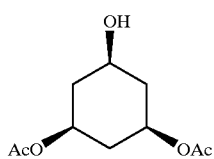

3

(b) reacting a compound of formula 3 with tert-butyldimethylsilylchloride in an organic solvent in the presence of an organic base at a temperature ranging from −15 to 20° C. for a period ranging from 6 to 12 hrs, separating the organic solvent, drying and on evaporation to obtain cis,cis-3-(methylcarbonyloxy)-5-(tert.butyldimethylsilyloxy)cyclohexylacetate having formula 4,

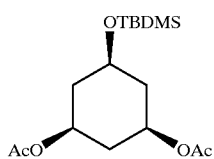

4

(c) reacting a compound 4 with a lipase enzyme in a buffer having pH in the range of 5 to 8, at a temperature ranging from 25 to 30° C. for a period ranging between 24 to 60 hrs., extracting the mixture with an organic solvent, removing the solvent by evaporation and on column chromatography to obtain 3-hydroxy-5-(tert.butyldimethylsilyloxy)-(1S,3R,5R)-cyclohexylace-tate having formula 5,

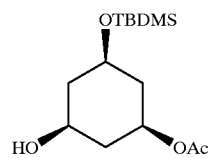

5

(d) reacting a compound of formula 5 with dihydropyran in an organic solvent in the presence of p-toluene sulphonic acid at a temperature ranging from 5 to −10° C. for a period ranging from 2 to 5 hrs, quenching the above reaction with an aqueous sodium bicarbonate, separating the organic layer, drying, on evaporating and column chromatography to obtain 3-tetrahydro-2H-2-pyranyloxy-5-(tert.butyldimethylsilyloxy)-(1S,3R,5R)-cyclohexylacetate having formula 6,

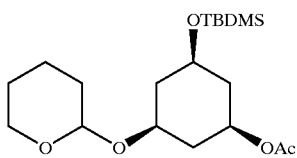

6

(e) reacting a compound of formula 6 with an anhydrous potassium carbonate in methanol at room temperature for a period ranging from 2 to 6 hrs, evaporating the solvent, extracting with an organic solvent, washing with brine solution, drying, evaporating and column chromatography to obtain 3-tetrahydro-2H-2-pyranyloxy-5-(tert.butyldimethylsilyloxy)-(1S,3R,5R)-cyclohexan-1-ol having formula 7,

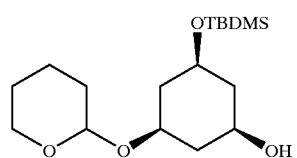

7

(f) reacting a compound of formula 7 with pyridinium chlorochromate in an organic solvent at room temperature for a period ranging from 6 to 8 hours, extracting the above mixture with an ether, washing with brine, drying, on evaporating and column chromatography to obtain 3-tetrahydro-2H-2-pyranyloxy-5-(tert.butyldimethylsilyloxy)-(1S,3R,5R)-cyclohexan-1-one having formula 8,

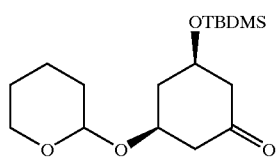

8

(g) reacting a compound of formula 8 with magnesium bromide in an organic solvent at a temperature ranging from 5 to 30° C. for a period ranging from 1 to 12 hours, quenching the above reaction ammonium chloride, separating the organic layer, drying and on evaporating to obtain 3-hydroxy-5-(tert-butyldimethylsilyloxy)-(3S,5R)-cyclohexan-1-one having formula 9,

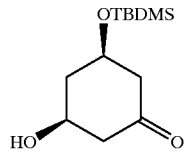

9

(h) reacting a compound of formula 9 with m-chloroperbenzoic acid at room temperature for a period ranging from 16–24 hours, extracting the compound with an orgainc layer, washing with sodium metabisulphite, brine, drying and on evaporation to obtain 6-hydroxymethyl-4-(tert-butyldimethylsilyloxy)-(4R,6S)-tetrahydro-2H-2-pyranone having formula 1.

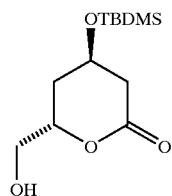

2. A process as claimed in claim 1, wherein the organic solvent used in steps a, c, e and h for the extraction of the product is selected from the group consisting of ethyl acetate, chloroform, dichloromethane and t-butanol.

3. A process as claimed in claim 1, wherein the organic solvent used in steps b, e, f and g for the reaction is selected from the group consisting of ethyl acetate, chloroform, dichloromethane, methanol and diethyl ether.

4. A process as claimed in claim 1, wherein the organic base used in step b for the reaction is selected from triethylamine and pyridine.

5. A process as claimed in claim 1, wherein the buffer used in steps a and c for the reaction is selected from phosphate buffer and citrate buffer.

6. A process as claimed in claim 1, wherein the lipase used in steps a and c for the reaction is selected from the group consisting of pig procain lipase (PPL), pig liver esterase (PLE) and chicken liver acetone powder (CLAP).

7. A compound cis,cis-3-hydroxy-5-methylcarbonyloxy-cyclohexylacetate having formula (3).

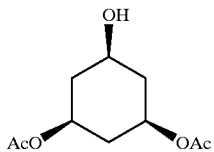

8. A compound cis,cis-3-(methylcarbonyloxy)-5-tert.butyldimethylsilyloxy)cyclohexylacetate having formula 4.

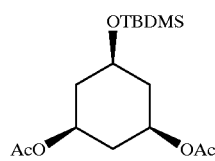

9. A compound 3-hydroxy-5-(tert.butyldimethylsilyloxy)-(1S,3R,5R)-cyclohexylacetate having formula 5

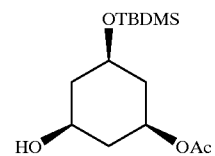

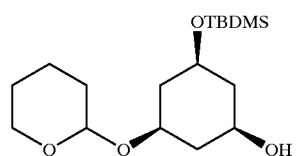

10. A compound 3-tetrahydro-2H-2-pyranyloxy-5-(tert.butyldimethylsilyloxy)-(1S,3,R5R)-cyclohexan-1-one having formula 8.

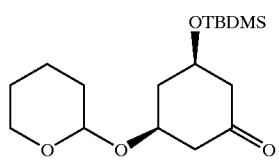

11. A compound 3-hydroxy-5-(tert-butyldimethylsilyloxy)-(3S,5R)-cyclohexan-1-one having formula 9.

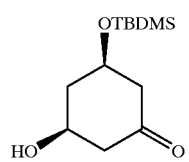

* * * * *